United States Patent [19]

Stroetmann

[11] 4,442,655

[45] Apr. 17, 1984

[54] FIBRINOGEN-CONTAINING DRY PREPARATION, MANUFACTURE AND USE THEREOF

[75] Inventor: Michael Stroetmann, Münster, Fed. Rep. of Germany

[73] Assignee: Serapharm Michael Stroetmann, Münster, Fed. Rep. of Germany

[21] Appl. No.: 392,215

[22] Filed: Jun. 25, 1982

[30] Foreign Application Priority Data

| | | |
|---|---|---|
| Jun. 25, 1981 [DE] | Fed. Rep. of Germany | 3124962 |
| Jun. 25, 1981 [DE] | Fed. Rep. of Germany | 3124933 |
| Aug. 12, 1981 [DE] | Fed. Rep. of Germany | 3131827 |
| Dec. 18, 1981 [EP] | European Pat. Off. | 81110615 |
| May 26, 1982 [EP] | European Pat. Off. | 82104606 |

[51] Int. Cl.$^3$ ............... A61K 9/14; A61K 35/14; A61K 37/00
[52] U.S. Cl. ................ 53/428; 106/124; 424/101; 424/124; 424/177; 424/359; 53/440; 424/27
[58] Field of Search ............... 424/101, 177, 27, 359, 424/124; 106/124; 53/428

[56] References Cited

U.S. PATENT DOCUMENTS

| | | | |
|---|---|---|---|
| 2,492,458 | 12/1949 | Bering | 424/101 |
| 3,523,807 | 8/1970 | Gerendas | 106/124 |
| 3,928,566 | 12/1975 | Briggs et al. | 424/101 |
| 4,113,853 | 9/1978 | Funakoshi et al. | 424/101 |
| 4,298,598 | 11/1981 | Schwarz et al. | 424/101 |
| 4,362,567 | 12/1982 | Schwarz | 424/101 |

OTHER PUBLICATIONS

Chem. Abst. 90:101,085V, Bruhn (1979).
Chem. Abst. 89: 117,741w, Stemberger, A. Thromb. Res. 1978 12(5) pp. 907–910.
Chem. Abst. 95: 225,618u, Haverich Thorac Cardiovas Surg. 1981.
Schwarz et al.–Chem. Abst. vol. 94 (1981), p. 36318q.
Schwarz et al.–Chem. Abst. vol. 94 (1981) p. 36384h.
McKendrick et al.–Chem. Abst. vol. 76 (1972) p. 17809n.

*Primary Examiner*—Theodore Morris
*Attorney, Agent, or Firm*—Gordon W. Hueschen

[57] ABSTRACT

A dry preparation having a foam-like and, respectively, fleece-like structure obtained by freeze-drying consists, apart from thrombin in at least catalytically active amounts, substantially of approx. 10 to 95% by weight of fibrin and approx. 5 to 90% by weight of fibrinogen. For the preparation thereof, fibrin is produced in situ in an aqueous solution containing fibrinogen and thrombin and the resultant reaction mixture is deep-frozen and lyophilized. As further constituents of the dry preparation active substances such as e.g. antibiotics, natural bone material and/or a synthetic, bone-forming substitute, glycoproteins, coagulation-conducive substances and the like and/or fibrinolysis inhibitors come into consideration. The dry preparation is provided mainly for use as a wound toilet material, as a filling material for bone cavities and/or as a supporting material for further active substances.

18 Claims, No Drawings

FIBRINOGEN-CONTAINING DRY PREPARATION, MANUFACTURE AND USE THEREOF

The present invention relates to a fibrinogen-containing dry preparation having a foam-like and fleece-like structure, respectively, obtained by freeze-drying. Such a dry preparation, which is completely resorptive, may in particular be used as a wound toilet material, as a filling material for pathological bone cavities and/or as a supporting material for further active substances conducive to a healing process. Furthermore, the invention relates to a process of manufacturing this dry preparation and to the use thereof.

A dry preparation of the mentioned type is known from the German Laid-Open Patent Application No. 30 37 513, which concerns a collagenic wound cover obtained by freeze-drying of a solution containing both collagen and fibrinogen. The resultant dry material may additionally contain a pharmaceutically-active substance such as an antibiotic. A considerable content of collagen in a wound cover—especially when the same shall be resorbed—may be harmful, as will be shown in the following.

Furthermore, a lyophilized tissue adhesive (cf. German Laid-Open Patent Application No. 30 02 934) is known which substantially—apart from a fibrinolysis inhibitor and factor XIII—may consist of fibrinogen and albumin and additionally contain glycine, glucose and heparin. However, this tissue adhesive shall not be applied onto the wound in the form of a dry preparation but shall be reconstituted by adding water so as to obtain a concentrated fibrinogen solution to which then thrombin and $CaCl_2$ are added.

Furthermore, from the German Laid-Open Patent Application No. 28 52 319 an absorbable haemostatic substance for use in combatting bone haemorrhages is known, which in a water-soluble, bio-compatible base comprises a haemostatic powder, viz. a mixture of fibrin and collagen powder.

Finally, from the U.S. Pat. No. 3,523,807 shaped articles are known, which after implantation are completely resorptive and which substantially are made of fibrin. For the manufacture thereof, fibrin is separated from plasma by adding calcium chloride, the precipitate is dried and pulverized, if desired, the resultant powder is mixed with another powdery protein, the powder is made into a paste with water and is pressed in a mold to obtain the desired shaped article, which, thereafter, is hardened in a bath containing formaldehyde.

The freeze-drying (lyophilization) of aqueous protein solutions is known among those skilled in the art. A loose, foam-, felt- or fleece-like structure having numerous cavities is obtained, which has the consequence that such a dry preparation has a high absorptive capacity relative to body fluids. The preparation of a collagen product having a felt-like and, respectively, fleece-like fiber structure by freeze-drying of an aqueous collagen solution is described e.g. in the German Laid-Open Patent Application No. 26 25 289. Such dry collagen preparations distinguish themselves by a high mechanical strength so that such collagen fleeces may be cut and bent.

If, however, under comparable conditions, an aqueous fibrinogen solution were processed by freeze-drying to obtain a dry preparation, a protein plate having a foam-like structure would be obtained which breaks and crumbles easily. Due to its insufficient mechanical strength, such a plate would be unsuited as a wound toilet material and/or supporting material for pharmaceutical active substances.

In spite of their haemostatic effect and high stability (mechanical strength, storage stability), freeze-dried and other collagen products have not been entirely satisfactory in practice when being used as a wound toilet material and/or resorptive implant. Drawbacks are e.g. the long residence time of up to six weeks and more in the wound area and undesired effects of collagen on certain healing processes, e.g. in the case of bone fractures. Frequently, known collagen preparations have been denatured in the course of their separation from natural material and their preparation, so that this has resulted in an insoluble preparation having a poor resorption behaviour. In contrast thereto, readily soluble collagen preparations always contain salts causing an acidic pH. After introduction into a wound, such collagen preparations, in their turn, cause therein an acidic environment, the neutralization of which is an unnecessary burden to the organism and impairs the healing process. It is exactly wound healing and the thrombin-induced fibrin formation from present soluble fibrinogen which require for their optimum progress an environment having a physiological pH of approx. 7.36. Finally, in the wound area collagen is already present in the endogenic structures, tissues and fluids in a physiologically utilizable form so that a considerable additional collagen offer is neither necessary nor desirable.

Natural wound closure material is a fibrin of gel-like state formed from fibrinogen and still having a large content of native fibrinogen. The in vitro provision of a dry preparation which is more similar to the natural wound closure material than conventional dry collagen preparations and which nevertheless has the advantageous properties of such collagen preparations, such as e.g. high mechanical strength, good absorptive capacity and great fluid-retaining capacity as well as unlimited storage stability at room temperature, would lead to a considerable improvement in medical care.

Based thereon, it is the object of the present invention to provide a fibrinogen-containing dry preparation of the above-specified kind, which is entirely or substantially free from collagen and nevertheless has the advantageous properties of common collagen preparations, which, regarding its composition, its physiological properties and its resorption behaviour is more similar to natural wound closure material and which is directly, i.e. without any further manipulations such as e.g. the addition of additional and/or activating components, applicable onto the wound and effects an accelerated haemostasis at the wound.

According to the invention this object is solved by a fleece obtained by freeze-drying which, apart from thrombin in at least catalytically effective amounts, substantially consists of approx. 10 to 95% by weight of fibrin and approx. 5 to 90% by weight of fibrinogen.

The process according to the invention for manufacturing such a dry preparation provides preparing fibrin in situ in an aqueous solution containing fibrinogen and thrombin and freeze-drying and lyophilizing the resultant reaction mixture.

A further aspect of the invention relates to the use of such a dry preparation for accelerated haemostasis and optimized biochemical control of wound closure as well as for the treatment of osteomyelitis. Furthermore, the dry preparation may be employed for the most varied applications as a supporting material and, respectively, as an active substance depot for any active substances conducive to a healing process. Regarding quantity and duration, the release of the active substance from the dry preparation may be controlled by its fibrin content, by additional components as well as by a predetermined degree of cross-linkage and/or polymerization of the fibrin.

Advantageous modifications and further embodiments of the invention are apparent from the subclaims.

The invention is based on the observation that by freeze-drying of a reaction mixture which, apart from fibrinogen and at least catalytic amounts of thrombin, contains fibrin formed in situ, a dry preparation is obtained which has a surprisingly high stability, comparable with the stability of freeze-dried collagen products. Even without the addition of further substances and factors conducive to blood coagulation, such a dry preparation has a particularly high hemostatic activity, especially due to the additional offer of active thrombin and fibrinogen. Preferably, the fibrin offered with the dry preparation and formed in situ is an especially dimerized fibrin of high biological activity, which is cross-linked only in its longitudinal direction, i.e. is linked substantially only through its $\gamma$-chains, and which is used as a starting point for a further and intensified fibrin formation in the wound area. With the dry preparation according to the invention a component mixture may be offered which is very similar to the natural wound closure material and which consequently is readily adopted by the organism and completely resorbed. A dry preparation formulated in accordance with the invention as a wound closure material, e.g. in the form of a fleece having a thickness of 6 to 20 mm, can also stop heavy haemorrhages within a short time, approx. within 2 min.

For manufacturing the dry preparation according to the invention, one starts from an aqueous or predominantly aqueous solution. This initial solution may be water, human serum or an aqueous salt solution. The aqueous salt solution may be a physiological saline or a physiological saline additionally enriched with $CaCl_2$ and phosphate salts. The pH and the salt content of this initial solution shall largely correspond to the physiological conditions. In some cases, it may be suitable to use a predominantly aqueous solution, which, apart from water, contains water-soluble, organic solvents, e.g. in order to increase the solubility relative to certain active pharmaceutical substances. Suitable organic solvents include monohydric alcohols such as ethanol or isopropanol, polyhydric alcohols such as glycerol or polyglycols, cyclic ethers such as dioxane and the like. The maximum content of organic solvents is selected so that there will be no denaturing and/or decrease in activity of the employed enzymes and that the drying of the frozen substance will not be impaired. Mostly, the proportion of organic solvent shall not exceed 20% of the volume of the total formulation.

Human fibrinogen is added to the initial solution. Suitable preparations are commercially available and may e.g. be obtained from the company Behring-Werke, Marburg. Furthermore, a well suited fibrinogen preparation may be obtained according to the following process.

Human plasma is cooled to 4° C. and $\beta$-alanine (2 molar solution in ethanol) is added thereto with agitation until with further ethanol addition the raw fibrinogen precipitates. This raw fibrinogen is centrifuged off, dissolved in 0.01 M of tris buffer (pH 7.4) and again precipitated by adding 2 M of glycine. The isolated sediment is dissolved in an 0.9% aqueous NaCl solution, dialized relative to the same solvent, desalted and subsequently lyophilized. The resultant microcrystalline fibrinogen has a molecular weight of $340,000 \pm 5\%$, is slightly digested partially in the $\alpha$-chain, quickly dissolves after introduction into body fluid and immediately thereupon starts to polymerize. The proportion of fibrinogen which is coagulatable in solution amounts to at least 85%.

To the above-mentioned initial solution, which preferably is held at room temperature, approx. 10 to 90 mg. of fibrinogen are added per 1 ml of solution. Preferably, a relatively high fibrinogen concentration of approx. 50 to 80 mg/ml is provided. Provided there is no foaming of the solution, the preparation obtained after freeze-drying substantially will have the volume of the initial solution. Therefore, an increased fibrinogen concentration in the initial solution leads to a denser end product of higher mechanical strength.

The added fibrinogen is dissolved in the initial solution, for which purpose agitation may be carried out at room temperature.

According to an alternative process it is not necessary first to isolate the fibrinogen in pure, solid form and then to add it to an aqueous solution. E.g., the sediment described in connection with the above-mentioned fibrinogen isolation and obtained after the glycine precipitation may be dissolved in an 0.9% aqueous NaCl solution and adjusted to the desired degree of concentration, and, as will be explained in the following, the further additives may be added directly to this solution. Also other fibrinogen solutions are suited, for the preparation of which the raw fibrinogen has been isolated as a cryoprecipitate from the remaining serum with its proteins and factors, e.g. according to the process of the German Laid-Open Patent Application No. 30 02 934. What is important is a far-reaching isolation of the enzymes and/or factors causing the spontaneous fibrin formation, so that a considerable content of stabilizing salts such as citrate, phosphate, oxalate or the like is prevented in the initial solution. It is exactly the dry preparation provided as a wound closure material which shall provide a component mixture which is very similar to the natural wound closure material. In particular for this application unphysiological salt concentrations in the initial fibrinogen solution are to be prevented. On the other hand, when providing this initial solution, one may already aim at an enrichment with coagulation factors, e.g. factor XIII. The fibrinogen content of such an initial fibrinogen solution shall also amount of 10 to 90 mg, preferably to 50 to 80 mg of fibrinogen per 1 ml of solution.

The fibrinogen solution obtained according to the one or the other process may be sterilized, in particular be treated specifically to inactivate viruses such as hepatitis viruses. For this purpose, e.g. a treatment with $\beta$-propiolactone, followed by ultraviolet irradiation, may be provided. Alternatively, sterilization with high-energy $\gamma$- or X-radiation may be provided.

Subsequently, the selectively provided additives and active substances may be added to the fibrinogen solution.

The flexibility, mechanical strength and stability of the dry preparation may be controlled by admixing various glycoproteins. For this purpose, one or more glycoproteins such as albumin, lipoprotein, fibronectin and/or globulin (α-, β-, γ-globulins) may be added to the fibrinogen solution. For these glycoproteins a proportion of approx. 3 to 40, preferably approx. 5 to 25% by weight of the finished dry preparation may be provided. Such glycoproteins also serve as desiccants and stabilizers and prevent a loss of activity of the coagulation enzymes during long periods of storage.

If the dry preparation is specifically used as a supporting material or as a depot material for certain active substances, these may also be added to the fibrinogen solution provided they are water-soluble and not impaired by the freeze-drying. The term "active substance" is meant in a very wide sense and includes all compositions which are parenterally active for healing, mitigating, treating and/or preventing disturbances of health in man and animal or which may influence the functioning of the organism. In this respect, mainly antibacterial active substances, especially antibiotics, come into consideration. Suitable antibiotics e.g. are the group of the amino-glycoside antibiotics such as e.g. gentamicin, the lactone antibiotics such as e.g. novobiocin, the group of the penicillins such as e.g. Baycillin or amoxicillin, the chloramphenicol and the derivatives thereof such as e.g. tiamphenicol and other antibiotics such as e.g. the group of the streptomycins, the group of the tetracyclines and the like. Further suitable antibacterial active substances e.g. are the sulphonamides. Due to their wide range of action, the amino-glycoside antibiotics, here especially gentamicin, are preferred particularly. Furthermore, a combination of different antibiotics, e.g. gentamicin together with tetracycline, may be provided. Further suitable active substances for other indications include the antiseptics such as e.g. salicylic acid or undecenoic acid, the anti-inflammatory substances such as e.g. pyrazolones, and, furthermore, the cytostatic drugs such as e.g. prednisone.

The amount of these active substances may vary within wide ranges and mainly depends on the activity of the active substances. Based on the total weight of the dry product, the active substance content may amount to approx. 0.1 to 10% by weight, preferably approx. 2 to 6% by weight. E.g. a gentamicin addition of approx. 500 to 10,000 units per 1 ml of fibrinogen solution has proven to be particularly suited.

Provided the dry preparation shall specifically be introduced into bone cavities so as to act therein as an active substance depot with time and quantity controlled active substance release and, at the same time, to contribute to the bone reformation, additives specifically conducive to the growth of bone may be provided. These include e.g. natural fine-particle bone material such as denatured bone meal or lyophilized bond particles pulverized subsequently, and/or a synthetic, bone-forming substitute such as e.g. inorganic salts of potassium, magnesium and calcium, especially calcium phosphate and here with particular preference tricalcium orthophosphate. For this particular purpose of application, the amount of additives conducive to the growth of bone may be selectived to be relatively high and preferably amount to approx. 50% by weight of the finished dry preparation.

In connection with the specified active substances an additive may be provided which effects a time and quantity control of the active substance release. Effective additives of this kind include collagen and cross-linked fibrin. The effectiveness of these additives depends on the affinity for the selected active substance. For numerous active substances, in particular the important group of the antibiotics and here, in particular, gentamicin, a proportion of additives controlling the active substance release of approx. 2 to 12% by weight, preferably of approx. 4 to 10% by weight based on the total weight of the dry preparation, has proven to be sufficient. For this purpose, a content of collagen of approx. 0.5 to 1% by weight is particularly preferred. To this end, a suitable amount of water-soluble collagen may be added to the fibrinogen solution, or the fibrinogen may be dissolved in a corresponding aqueous collagen solution. Such amounts of collagen are readily soluble in the total formulation, so that the above-mentioned difficulties (acidic pH and/or unphysiological salt concentrations) do not arise. Furthermore, the active substance release may be influenced by the content of fibrin and/or the extent of the fibrin cross-linking. Mostly, a high content of fibrin as well as a greater fibrin cross-linking delay the release of the active substances. A suitable fibrin cross-linking may be effected e.g. by adding glutaraldehyde.

If the dry preparation is to be used specifically as a wound toilet material, a freeze-dried fleece of average hemostatic effectiveness may be produced, to which later a highly effective, enriched, powdery plasma derivative is added for accelerated hemostasis and optimized control of wound closure, as will be set out in detail in the following. Alternatively, the essential components of this enriched plasma derivative may be added already to the fibrinogen solution. The main constituents of this plasma derivative include fibrinogen, thrombin, components of the prothrombin complex and protease inhibitors; furthermore, admixtures of blood platelet extracts, antibiotics and the like may be provided. In particular, an addition of phospholipids, prostaglandines, coagulation factors, antihistamines, vasopressins, growth factors, vitamins and the like may be provided for this purpose. The presence of prostaglandines contributes to the activation of the capillary bed in the wound area as well as the activation of the platelets in the blood stream. The blood coagulation factors, e.g. factor XIII, blood platelet extracts and other factors which are necessary for the coagulation of the blood such as e.g. leucotrines, platelet-activating factors, support and increase the effect of the factors present in the body fluid in the sense of an accelerated hemostasis and an optimization of wound closure. As the phospholipid preferably a thrombocyte extract obtained from human whole blood is used. Further suitable phospholipids are e.g. extracts from cerebral matter. The coagulation factors VIII and IX are used for hemophilic wound toilet. An additive of adrenaline and/or ergotamine has a vasoactive effect, which finally leads to an accelerated coagulation of the blood. With regard to their high specific effectiveness, the sum of the proportions of prostaglandines, phospholipids, coagulation factors and the further active substances mentioned mostly is not more than 1.2% by weight, preferably not more than 0.8% by weight of the finished dry preparation. The specified substances, in the mentioned amounts, are also added to the fibrinogen solution prior to or together with the addition of thrombin.

Furthermore, a fibrinolysis inhibitor may be added. Preferably, a relatively great proportion of fibrinolysis inhibitor is provided, viz. at least 5,000 units (so-called kallikrein inactivator units), preferably, however, 10,000 and more units of fibrinolysis inhibitor per 1 ml of solution. Fibrinolysis inhibitors coming into consideration are e.g. a plasminogen-activator inhibitor or one of more antiplasmins such as e.g. $\alpha_1$-antiplasmin, $\alpha_2$-macroglobulin or aprotinin as well as $\epsilon$-aminocaproic acid and/or trypsin inhibitor. E.g. the natural fibrinolysis inhibitor sold by Bayer AG, Leverkusen, under the tradename "Trasylol" has proven to be particularly suited.

After adding of one or more of the mentioned or of other active substances selected with regard to a predetermined purpose of application to the finbrinogen solution and complete or substantial dissolution therein, thrombin is added. As is known, thrombin can separate the fibrinopeptides A and B from a fibrinogen molecule, whereby a fibrin monomer is obtained which then spontaneously reacts with other fibrin monomers so that finally a polymer of fibrin molecules is obtained. The added thrombin shall under known, standardized conditions have at least a biological activity of 10,000 units (NIH units according to the standards of the National Institute of Health of the United States) per 1 mg. of thrombin. Suitable preparations are commercially available. E.g. a suitable thrombin in microcrystalline form having a biological activity of at least 3,000 units/mg of the preparation (which apart from thrombin comprises known stabilizers and supporting materials) can be obtained under the tradename "Topostasin" from Hoffmann LaRoche, Grenzach, Baden.

Part of the desired thrombin activity may also be added in the form of thrombin-forming precursors such as e.g. prothrombin. Prothombin concentrates are also commercially available, e.g. as PPSB preparations of the company Immuno AG, Vienna. Furthermore, a combined preparation containing thrombin and prothrombin may be separated from a commercially available prothombin complex by column chromatography or be extracted from human plasma by means of barium sulfate and recovered from the crystalline precipitate.

The proportion of added active thrombin depends on various factors. Regarding the process conditions, a high thrombin concentration accelerates the fibrin formation so that in the case of high thrombin concentrations the reaction mixture must be deep-frozen after a relatively short period of time so as still to ensure a sufficient fibrinogen content. As regards the end product and the various applications thereof, a relatively high thrombin content is desirable for a wound toilet material for accelerating the hemostasis together with the additional fibrinogen offer. For producing a wound toilet material which has a satisfactory hemostatic effect also without later addition of coagulation-active enzymes and factors, relatively high amounts of thrombin, may be added to the fibrinogen solution, e.g. 20 to 30 and more units of thrombin per 1 ml of solution. For other cases of application, e.g. as a supporting material for active substances such as antibiotics, the thrombin content of the end product is of minor importance; in this case, a small thrombin addition will be sufficient which is enough for reacting the provided fibrinogen into fibrin to the desired high amount of more than 50% within adequate periods of time. In this case, catalytically active amounts of thrombin of at least 0.1 unit, preferably of approx. 5 to 10 units per 1 ml of fibrinogen solution, will be sufficient.

If there are no unphysiologically high salt and/or stabilizer concentrations, thrombin generates from fibrinogen fibrin monomers which are polymerizable in an aqueous medium. The nature of the polymer obtained from these monomers depends on various factors. If the fibrinogen-and thrombin-containing formulation were left to itself, the entire fibrinogen would be reacted after approx. 4 to 6 hours and a stiff gel would be obtained which, when being shaken, collapses into fibrin filaments. In this case, the polymerization takes place through the $\alpha$- and $\gamma$-chains of the fibrin monomers. If the resultant precipitate were lyophilized, a hard, brittle product would be obtained, which is less suited as a wound toilet material due to its low mechanical strength and flexibility as well as its reduced solubility and delayed degradability.

The exclusive polymerization of the fibrin monomers yields a soluble polymer of little stability, which predominantly is stabilized by hydrogen bridge bonds, electrostatic interactions, hydration and the like. An increased stability results from the formation of covalent bonds between neighbouring fibrin molecules. As is known, this requires the presence of factor XIII, which, in its turn, is activated by thrombin in the presence of $CaCl_2$. Depending on the conditions of preparation, solid or dissolved fibrinogen practically always contains a smaller or greater amount of factor XIII. Frequently, the separation of raw fibrinogen from the plasma is carried out under such conditions that also factor XIII is separated together with the raw fibrinogen. The production of covalent conditions may take place in the various side chains of neighbouring fibrin molecules, which to a different extent contribute to the cross-linking of the fibrin polymer in longitudinal and transverse direction.

It has been realized within the scope of the invention that a soluble fibrin polymer predominantly cross-linked in longitudinal direction may be obtained if the production of covalent bonds is discontinued in good time since the covalent bonds necessary for the cross-linking in transverse direction are formed at a lower rate than the covalent bonds required for the cross-linking in longitudinal direction. The starting of the cross-linking in transverse direction becomes noticeable by a marked increase in viscosity of the formulation. For controlling the terminated $\gamma$-chain dimerization, the viscosity of the fibrinogen/fibrin monomer solution may be monitored. If the reaction is not discontinued in due time, the viscosity under the action of the $\alpha$-chain polymerization may reach the tenfold of the viscosity of the initial solution. A fibrinogen/fibrin monomer solution is well suited for the manufacture of a dry preparation according to the invention if the viscosity of said solution has reached twice the value of the initial viscosity, because then the $\gamma$-chain dimerization has substantially been terminated and the $\alpha$-chain polymerization has not yet started appreciably. Depending on the thrombin and the factor XIII concentration, the doubling of the starting viscosity, as a rule, is reached 30 to 40 min. after the thrombin addition.

For many cases of application, especially as a wound toilet material, a fibrin polymer predominantly cross-linked in longitudinal direction is desirable since this fibrin polymer is more readily soluble, has a greater physiological activity and contains large amounts of thrombin in bonded form and therefore is aimed at for the sake of a rapid coagulation of the blood. Furthermore, exactly such a fibrin predominantly cross-linked in longitudinal direction, viz. predominantly only $\gamma$-chain-dimerized fibrin, may be foamed in the solution or cross-linked in accordance with the requirements by adding glutaraldehyde.

As a basis for the extent of the cross-linkage of the fibrin polymer in transverse and longitudinal direction, the α-polymer and γ-dimer formation may be measured. For this purpose, a fibrin mixture is dissolved in a sodium-lauryl-sulphate-containing buffer with additives of mercaptoethanol and separated electrophoretically in polyacrylamide gels.

If a fibrin polymer predominantly cross-linked in longitudinal direction is aimed at, the reaction period of the formulation after adding of thrombin shall be limited to a maximum of 40 min. Preferably, after the adding of thrombin, a reaction period of approx. 10 to 30 min. is provided. Under these conditions, a fibrin polymer is obtained which predominantly contains γ-chain dimers and is substantially free from α-chain polymers. Additionally, the fibrin formation may be carried out in the presence of SH-group blocking substances such as e.g. iodine acetate. This increases the proportion of fibrin which is present in the form of fibrin monomers.

Irrespective thereof, for some cases of application a higher degree of cross-linking in transverse direction may also be desirable, especially if the dry preparation is to have a particularly high fibrin content of more than 80% by weight. A high degree of cross-linking in transverse direction further yields a denser structure and increases the residence time of the dry preparation in the tissue. If a higher degree of cross-linking in trans- direction is desired, the reaction period after the thrombin addition may also amount to more than 40 min. and be extended to several hours. The dry preparation obtained after the freeze-drying of the gels resulting therein shall also be covered by the present invention. In this case, it is desirable to avoid a destruction of the gel structure; therefore, the formulation is put into the freeze-drying mold immediately after the thrombin addition and brief agitation, is maintained unmovedly at room temperature for the provided reaction period and thereupon is cooled rapidly.

Moreover, the cross-linkage of the fibrin polymer may also be controlled by the addition of cross-linking agents. Suitable cross-linking agents include e.g. bivalent, bridging substances such as e.g. SPDP, viz. N-succinimidyl-3-(2-pyridyl-dithio)-propionate, or bivalent organic substances generating with the present amino groups peptide bonds, such as e.g. formaldehyde, glutaraldehyde, malonyldialdehyde, adipic acid and/or the derivatives thereof. In view of the high effectiveness thereof, the added amount of cross-linking agent may be kept rather low and e.g. amount to only 0.1 to 5% of the entire formulation. E.g. an addition of 3 ml of glutaraldehyde to a 100 ml formulation has proven to be particularly suited. Such a cross-linkage also increases the tensile and breaking strength of the formed dry preparation.

Thus, according to the invention of the fibrin contained in the dry preparation is prepared in situ in an aqueous medium containing fibrinogen and thrombin. The fibrin formed in this manner proves to be much more native, soluble and purer than e.g. the fibrin according to the U.S. Pat. No. 3,523,807, which by $CaCl_2$ precipitation is precipitated from human plasma and separated. The latter material is practically insoluble, contains inclusions of other plasma proteins and thus is less suited for application as a wound toilet material.

Preferably, the in situ formation of fibrin is carried out under such conditions that the resultant fibrin polymer comprises covalent bonds between neighbouring fibrin molecules. To this end, the reaction mixture shall contain at least catalytically active amounts of factor XIII; preferably, 1 ml of reaction mixture shall contain at least 0.5 to 1 unit of factor XIII. What is particularly preferred is a fibrin polymer of this kind the covalent bonds of which predominantly have led to a cross-linkage in longitudinal direction, i.e. the proportion of the covalent bonds causing a cross-linkage in transverse direction relative to the total number of all covalent cross-linkages shall be less than 2%. The gel electrophoresis may be used as a basis for the degree of the cross-linking in transverse direction. The particularly preferred fibrin polymer is fibrin predominantly cross-linked in longitudinal direction due to its γ-chain dimerization. Major complexes may be prepared by belated polymerization and/or cross-linkage.

When the fibrin formation, polymerization and cross-linkage has progressed sufficiently, the formulation is deep-frozen. To this end, rapid cooling, e.g. within 5 min. to a temperature beneath $-20°$ C., preferably to $-40°$ C. or even lower temperatures is applied. The choice of the cooling temperature is not of critical importance since beneath $0°$ C. thrombin and the other coagulation factors practically have no appreciable activity.

The material is held at the cooling temperature until the entire formulation is frozen through and through into a solid ice body. Depending on the quantity of the formulation, a residence time of approx. 20 to 30 min. at $-40°$ C. in the freezing mold has proven to be particularly suited.

Subsequently, drying is carried out under known conditions. To this end, the ice body or bodies are put into a vacuum chamber and heated so slowly that the evaporating liquid can always be discharged and precipitated at a cold trap so that the deep-frozen product never liquefies. If a reduced pressure of less than 1 to 60 Pa is applied, the drying operation will be terminated in approx. 3 to 8 hours.

The resultant product is a loose mass of foam-, felt- or fleece-like structure. When examined under the microscope, with 200 times magnification, one will realize an interwoven network of fine fibers. The resultant fleece has the volume of the original liquid formulation and has a homogeneous, uniform composition within the entire fleece volume. Mostly, the specific weight of the fleece structure ranges between approx. 0.1 and 0.5 $g/cm^3$. If an even looser and lighter material is desired, the liquid formulation may be foamed prior to the filling into the freeze-drying mold. To this end, an inert propellant such as e.g. nitrogen or carbon dioxide is blown into the liquid. A predetermined pore size of the resultant foam may be adjusted by adding surface-active agents.

The outer dimensions of the fleece obtained after freeze-drying are adapted to the respective purpose of application. For use as a wound toilet material a fleece having a thickness of approx. 6 to 20 mm, a length of approx. 3 to 12 cm and a width of 1 to 12 cm has proven to be particularly suitable. In case the dry preparation preferably is to be used as an active substance depot and is to be implanted into the tissue or introduced into bone cavities, the use of pieces has proven to be particularly suited, e.g. of balls having a diameter of approx. 1 to 3 cm, cubes having an edge length of approx. 1 to 3 cm or discs, suppositories and the like with similar dimensions. For obtaining these outer dimensions, the liquid formulation is suitably filled into correspondingly shaped freeze-drying molds.

After termination of the drying operation, the dry preparation is carefully loosened at one edge from the hold bottom and pulled off. The resultant fleece is deposited on an Al-foil for a short time, cut to the desired dimensions, as far as necessary, and then placed into a recessed plastics container and the latter is closed with an Al-foil. Thereupon, the packaging including the content thereof may be sterilized, e.g. with x-radiation (dose: 3,000 rad for 3 min.). The product in the moisture-proof and sterile package may be stored at room temperature practically for an unlimited time, without any appreciable loss of activity.

As has already been mentioned, there are various possibilities of applying the dry preparation according to the invention and the composition of the dry preparation may specifically be adapted to the respective purpose of application.

According to the most general embodiment of the invention, the fleece, apart from thrombin in at least catalytically active amounts, shall substantially consist of approx. 10 to 95% by weight of fibrin and approx. 5 to 90% by weight of fibrinogen. By "at least catalytically active amounts" a thrombin content of approx. 0.1 to 10 units, preferably of 3 to 8 units, per 1 $cm^3$ of fleece material is meant. These "units" are the "NIH-units" (according to the standards of the National Institute of Health of the United States) common among those skilled in the art. In the case of a fibrin content of less than 10% by weight, the fibrinogen nature of the dry preparation is prevailing so that the material is brittle and has an insufficient mechanical strength. Therefore, the fibrin content shall amount to at least 10% by weight, preferably at least 30% by weight of the dry preparation. Fibrin contents of more than 95% by weight require reaction conditions which yield a solid material of physiologically low activity, which can be dissimilated by the organism only with difficulties. Therefore, the fibrin content shall not amount to more than 95% by weight, preferably not more than 70% by weight, of the weight of the fleece. A dry preparation having a fibrin content of approx. 20 to 30% by weight and a fibrinogen content of approx. 80 to 70% by weight, after moistening with body fluid, yields a preparation which is particularly similar to the natural wound closure material and thus is preferred especially.

If the dry preparation according to the invention mainly is to be used as a hemostatic and vulnerary wound toilet material, the fleece shall predominantly consist of fibrinogen. In this case, a fibrin content of approx. 10 to 40% by weight and fibrinogen content of approx. 60 to 90% by weight has proven to be particularly suited. On being moistened with the exudation of a wound, the wound toilet material shall take up the fluid, partially dissolve and form a highly viscous, sticky paste which adheres to the wound area, withstands the pressure of the escaping blood and activates the coagulation enzymes of the contacting blood. For this activation preferably coagulation-conducive substances, vasoactive substances, coagulation factors and the like are additionally offered with the dry preparation. These components may be introduced already into the solution used for the manufacture of the dry preparation and, together with the same, be deep-frozen and lyophilized. It is an advantage of this alternative that the components are most finely distributed within the dry preparation, which even further increases the effectiveness thereof. Alternatively, these components may belatedly be incorporated in the form of a powdery combination of active substances into the dry preparation substantially consisting only of thrombin, fibrin and fibrinogen. This permits the presence of active substances the activity of which is impaired by the freeze-drying and/or extraordinarily high thrombin concentrations which due to the accelerated fibrin formation would impair the process in other respects.

A suitable powdery biochemical substrate for accelerated hemostasis and optimized biochemical control of wound closure, which in powdery form may be applied onto the preformed dry preparation according to the invention, is described in detail in the European Patent Application No. 8 111 0615.2 of Dec. 18, 1981. As far as necessary, the content of this European Patent Application shall be incorporated into the present papers by reference. This powdery, biochemical substrate is formulated with regard to an optimized activation of the exogenic and/or endogenic coagulation system as well as under consideration of a multiplicity of physiological and pathological factors. This substrate contains inter al. fibrinogen, thrombin, components of the prothrombin complex, protease inhibitors. Depending on the purpose of application, additionally blood platelet extracts, antibiotics and the like may be added at suitable mixing ratios. A preferred embodiment of this plasma derivative consists substantially of 80 to 94% by weight of fibrinogen, 1 to 10% by weight of thrombin and/or prothrombin and 0.01 to 3% by weight of fibrinolysis inhibitor contains less than 0.4% by weight of cryo-insoluble globulin and, moreover, may additionally contain phospholipids, prostaglandines, desiccants and stabilizers, antibiotics and/or blood coagulation factors, all in solid, powdery form. This highly effective, powdery combination of active substances may be applied in amounts of approx. 0.1 to 5 parts by weight per 100 parts by weight of dry preparation. Preferably, these small amounts are blown onto the surface of the dry preparation by means of a sterile gas jet and adhere thereto in sufficient amount. The fibrin/fibrinogen fleece obtained thereafter may directly be used for wound treatment or be integrated into a first-aid bandage (adhesive plaster). Thus, a wound toilet material is obtained which has on the surface of an exclusively biological supporting material a highly effective active substance combination for accelerated hemostasis and optimized biochemical control of wound closure.

Furthermore, the dry preparation according to the invention may be used as a supporting material and, respectively, active substance depot for one or more active substance(s) conducive to some healing process or other. For this purpose of application, the dry preparation predominantly shall consist of fibrin. A high fibrin content ensures a high mechanical strength of the fleece, a sufficient residence time in the tissue and the desired active substance release over a prolonged period of time. Additionally, the presence of a constituent such as e.g. collagen, effecting a time and quantity control of the active substance release may be provided. Furthermore, the active substance release may be influenced by the kind and degree of fibrin cross-linkage. For this purpose of application, the supporting material preferably consists of approx. 65 to 95% by weight of fibrin and approx. 5 to 35% by weight of fibrinogen and contains additionally at least one active substance conducive to the healing process. Particularly good results were achieved with such a supporting material made of approx. 70 to 85% by weight of fibrin and approx. 15 to 30% by weight of fibrinogen. The active substance or active substances may be introduced already into the solution used for the manufacture of the dry preparation and be lyophilized together with the same or it may be introduced later into the lyophilized dry preparation.

A special field of application of such an active-substance containing fibrin/fibrinogen fleece is the treatment of osteomyelitis because the supporting material is completely resorptive and therefore a re-operation for removing the depot material is no longer required. In this case, the dry preparation suitably is formulated in the form of tablets, balls or other suitable shape and contains apart from antibiotics admixtures of calcium, protease inhibitors and factor XIII in any desired combination or at suitable mixing ratios so as to determine the resorption time and proteolytic degradability. Furthermore, an addition of growth factors, such as e.g. hormones and platelet extracts in therapeutically desired quantity and distribution may be provided.

In connection with bone fractures, it may be suitable to offer together with the active-substance containing dry preparation specifically also additives being conducive to bone regeneration. These include e.g. natural, fine-particle bone material such as e.g. denatured bone meal or lyophilized and pulverized bone particles or a synthetic, bone-forming substitute such as e.g. inorganic salts of potassium, magnesium and calcium, in particular calcium phosphate, wherein tricalcium orthophosphate is preferred particularly. Furthermore, active substances encouraging callus formation such as thrombocyte growth factors or hormones may be provided. For this special purpose of application, the dry preparation mainly consists of 30 to 45% by weight of fibrin, of approx. 4 to 15% by weight of fibrinogen, the balance being natural fine-particle bone material and/or a synthetic, bone-forming substitute as well as at least one antibacterial active substance. If necessary, this dry preparation may be introduced into the respective bone cavity together with sterilized, lyophilized, homologous bone fragments and/or with autologous spongiosa. In this manner, good filling and packing of bone cavities of any dimensions with the dry preparation according to the invention is possible due to its voluminous and flexible structure. The newly forming bony tissue may then with the gradual resorption of the fibrin network, germinate into the same, wherein the controlled active substance release ensures an antiseptic environment for a long period of time.

Thus, the present invention provides a supporting system of a fibrin mixture foam for taking up biochemical substances and substrates for accelerated hemostasis and optimized biochemical control of wound closure. The basic substance of the supporting system is a foam consisting of a mixture of fibrin and other substances. Depending on the respectively desired purposes of application, fibrin, thrombin, prothrombin, blood platelet extracts, protease inhibitors etc. are added to the fibrin mixture foam either individually or in any desired combination and at suitable mixing ratios. The admixture of proteins such as e.g. albumin, lipoprotein, fibrin, fibronectin and globulin permits the adjustment of the desired flexibility and stability of the foam. Depending on the purpose of application, especially fibrin, thrombin, prothrombin, blood platelet extract, protease inhibitors, antibiotics etc. may be added as admixtures to the fibrin-mixture foam individually, in a desired combination or at suitable mixing ratios. Furthermore, it is possible to add as admixture to the fibrin mixture foam a substrate or substrate complex for accelerated hemostasis and optimized chemical control of wound closure.

The following examples are intended to explain the invention in further detail without limiting it.

EXAMPLE 1

5 g of fibrinogen (microcrystalline preparation obtained from human plasma by alcohol/glycine precipitation, as specified above) are dissolved in 100 ml of 0.9% NaCl solution so as to obtain a resultant final concentration of protein of 50 mg/ml. 300 units of thrombin ("Topostasin" of the company Hoffmann LaRoche AG, Grenzach-Wyhlen) are added to the fibrinogen solution with agitation. Agitation is continued for a short time, and then the entire formulation is poured into a lyophilization mold and held at room temperature for further 20 min. Thereupon, deep-freezing follows, i.e. the entire formulation including the mold is cooled to approx. $-40°$ C. within 10 min. Thereupon, the formed ice block is lyophilized; for this purpose, the vapour phase is continuously pumped off under vacuum and freeze-separated. Thereby, a mixture of fibrinogen and soluble fibrin in the form of a loose, continuous protein fleece is obtained, which has a good mechanical and breaking strength. Apart from catalytically active amounts of thrombin, this dry preparation consists of approx. 20% by weight of fibrin and 80% by weight of fibrinogen. The following investigations were made with this dry preparation:

Determination of the fibrin content 1.0 g of the dry preparation is taken up with 10 ml of 0.9% NaCl solution, agitated and separated from insoluble constituents. The supernatant is separated into fibrin monomers and fibrinogen by gel electrophoresis with addition of sodium lauryl sulphate (without mercaptoethanol). The proportions are photometrically measured and determined after dyeing with Coomassie brilliant blue. There results a fibrin content of approx. 20% and a fibrinogen content of approx. 80%.

Determination of the fibrinogen activity 3 units of thrombin are added to 1 ml of the fibrinogen solution obtained according to the above-described process, the resultant fibrin is twisted about a rod and the remaining solution is separated. The extinctions prior to and after the fibrin separation may be determined in the photometer. Based on the determined value, the proportion of coagulatable fibrinogen was calculated to be more than 85% of the present fibrinogen.

Determination of the thrombin activity 1 g of the dry preparation is taken up in 10 ml of 0.9% NaCl solution and incubated at 37° C. The time till starting of the coagulation is measured. A reference solution with pure fibrinogen and increasing additions of thrombin is used as a standard for the determination of the thrombin activity in the lyophilisate. In the present case, approx. 35 to 45 units of thrombin could be detected.

For application as a wound toilet material the fibrinogen/fibrin fleece is cut to dimensions of $8 \times 50 \times 100$ mm and sterilized. In case of need, the product is placed onto the wound area. Due to the absorption of the exudation of the wound, the coagulation of the escaping blood is initiated.

EXAMPLE 2

9 g of fibrinogen are taken up in 100 ml of distilled water and 300 units of thrombin are added thereto. After pouring of the solution into the lyophilization mold, the progress of the reaction is observed and in the case of an appreciable increase in viscosity after approx. 20 min. the material is immediately deep-frozen. Due to the higher addition of thrombin, the proportion of soluble fibrin is increased to 40 to 50%.

EXAMPLE 3

9 g of fibrinogen are taken up by 100 ml of 0.1% collagen solution and 1 million units of gentamicin are added thereto. Additionally, the formulation also contains 100,000 units of Trasylol ®. To the thus prepared mixture 3,000 units of thrombin are added with agitation and it is poured into a lyophilization mold. After a reaction time of 6 hours, the content of the mold is deep-frozen and lyophilized.

EXAMPLE 4

5 g of fibrinogen are dissolved in 100 ml of a 1% albumin solution and 3 million units of gentamicin, 500,000 units of Trasylol ® and 3,000 units of thrombin are added thereto. After pouring into the lyophilization mold, 2 ml of glutaraldehyde are added as a cross-linking aid 20 min. later and the formulation is lyophilized.

EXAMPLE 5

9 g of fibrinogen are taken up in 100 ml of a 5% albumin solution. An amount of 5 million units of Baycillin ® and 1 million units of aprotinin are added to the formulation. After adding of 3,000 units of thrombin, the material is poured into an inert mold and deep-frozen after gelling. In this manner, it is possible to increase the proportion of fibrin to 85%. The lyophilized material yields a protein fleece having a compact structure, which when cut into cubes may well be employed for the toilet of infected bone marrow cavities.

EXAMPLE 6

5 g of fibrinogen are dissolved in 100 ml of 0.9% NaCl solution containing 0.025 M of $CaCl_2$. 1,0 g of albumin and 500 units of factor XIII are added to the formulation. As an antibiotic, the material shall contain 1 million units of Baycillin, which are added to the solution in the form of a powder. 100,000 units of aprotinin serve to prevent a premature lysis of the wound toilet material in the wound area. The inhibitor is also added to the solution in the form of a powder. By adding 30,000 units of thrombin, the fibrin formation is allowed to start, wherein the formulation exists already in dry form. After a reaction time of 1 hour, the material is freeze-dried. The adding of factor XIII increases the degree of cross-linkage of the fibrin and contributes to the stability of the fleece.

EXAMPLE 7

5 g of fibrinogen are added to 100 ml of plasma and dissolved with agitation. After adding of 300 units of thrombin, the mass gelling after 20 min. is put into a freeze-drying mold, deep-frozen and subsequently lyophilized.

EXAMPLE 8

5 g of fibrinogen are dissolved in 100 ml of 0.9% NaCl solution and 3,000 units of thrombin are added thereto. After 12 hours, the fibrin is converted by means of agitation from gel form into fiber form. The fibrous material is suspended in 5% albumin solution and its size is reduced mechanically. After adding of 2 ml of glutaraldehyde, the formulation is deep-frozen and subsequently lyophilized.

It is to be understood that the invention is not to be limited to the exact details of operations or to the exact compounds, compositions, methods, procedures, or embodiments shown and described, as numerous modifications and equivalents will be apparent to one skilled in the art and may be made without departing from the spirit or scope of the invention, which is therefore to be limited only by the full scope of the appended claims.

I claim:

1. Fibrinogen-containing dry preparation having a foam-like and fleece-like structure, especially adapted for use as a wound toilet material, filling material for bone cavities, and/or supporting material for further active substances, consisting essentially of thrombin in an at least catalytically active amount, about 10 to 95% by weight of fibrin, and about 5 to 90% by weight of fibrinogen.

2. Dry preparation according to claim 1, wherein 1 $cm^3$ of fleece material contains about 0.1 to 10 NIH units of thrombin.

3. Dry preparation according to claim 1, wherein the fleece is adapted mainly for use as a hemostatic and vulnerary wound toilet material, has a thrombin content of at least 1 NIH unit of thrombin per 1 $cm^3$ of fleece material, and contains about 10 to 40% by weight of fibrin, about 60 to 90% by weight of fibrinogen, and about 0 to 1.2% by weight of a material selected from the group consisting of coagulation-conducive substances, vaso-active substances, and coagulation factors.

4. Dry preparation according to claim 1 or 2, wherein the fleece is adapted mainly for use as a hemostatic and vulnerary wound toilet material, consists essentially of about 10 to 40% by weight of fibrin and about 60 to 90% by weight of fibrinogen, and comprises, incorporated into said fleece, a powdery enriched plasma derivative which is a combination of substances which accelerate hemostasis and optimize biochemical control of wound closure.

5. Dry preparation according to claim 1 or 2, wherein the fleece is adapted mainly for use as a supporting material and consists essentially of about 65 to 95% by weight of fibrin and about 5 to 35% by weight of fibrinogen, and additionally contains at least one active substance conducive to the healing process selected from the group consisting of antibiotics and antibacterial agents.

6. Dry preparation according to claim 1 or 2, wherein the fleece is adapted mainly for use as a filling material for pathological bone cavities and consists essentially of aboug 30 to 45% by weight of fibrin, and about 4 to 15% by weight of fibrinogen, the balance being selected from the group consisting of natural fine-particle bone material, synthetic bone-forming substitutes, and at least one anti-bacterial agent.

7. Dry preparation according to claim 5, wherein the fleece additionally contains a constituent effecting a time and quantity control of the active substance release.

8. Dry preparation according to any of claims 1, 2, or 3, wherein the fleece additionally contains one or more glycoproteins selected from the group consisting of albumin, lipoprotein, fibronectin, and globulin.

9. Dry preparation according to any of claims 1, 2, or 3, wherein the fibrin is essentially linked only through the γ-chains of the fibrin monomers.

10. Dry preparation according to any of claims 1, 2, or 3, wherein the fleece additionally contains one or more fibrinolysis inhibitors.

11. Process of manufacturing a dry preparation according to any of claims 1, 2, or 3, comprising the steps of preparing an aqueous solution containing fibrinogen and thrombin thereby to produce fibrin in situ, and deep-freezing and lyophilizing the resultant reaction mixture.

12. Process according to claim 11, wherein
(a) fibrinogen is added to water, human serum, or an aqueous salt solution;
(b) one or more active substances, additives, or the like are optionally added to the fibrinogen-containing solution;
(c) thrombin or a thrombin-forming precursor is added to the resultant solution;
(d) the mixture is reacted until part, but not the entire amount, of fibrinogen has reacted into fibrin monomers; followed by
(e) deep-freezing; and
(f) lyophilizing.

13. Process according to claim 11, wherein 10 to 90 mg of fibrinogen and 0.1 to 10 units of thrombin are added to the initial solution per each 1 ml of solution; agitation at room temperature is carried out for 10 to 40 min after the thrombin addition; the reaction mixture is cooled to a temperature below $-20°$ C.; and the formed ice is lyophilized without renewed formation of a liquid phase.

14. Process according to claim 11, wherein the fibrin formation is carried out (1) in the presence of substances blocking SH groups and/or (2) the fibrin mixture is cross-linked by the addition of a cross-linking agent.

15. Process according to claim 11, wherein the dry preparation is taken from the freezing mold and cut into shape, packaged moisture-proof, and the packaging including the content thereof is sterilized.

16. Method of using the dry preparation according to any of claims 1, 2 or 3 for accelerated hemostasis and optimized biochemical control of wound closure, comprising the step of applying onto the fibrin/fibrinogen fleece a powdery active substance combination containing fibrinogen, thrombin, components of the prothrombin complex, protease inhibitors, blood platelet extract and/or an antibiotic, and applying the thus-treated fleece to the wound.

17. Method of using the dry preparation according to any of claims 1, 2 or 3 for treating osteomyelitis, comprising the steps of providing the fibrin/fibrinogen fleece with any active substance required for the desired therapy and introducing the thru-treated fleece into the pathological bone cavity.

18. Method according to claim 17, wherein the fleece is in the form of small pieces, balls, or tablets.

* * * * *

UNITED STATES PATENT AND TRADEMARK OFFICE
CERTIFICATE OF CORRECTION

PATENT NO. : 4,442,655
DATED : April 17, 1984
INVENTOR(S) : Michael Stroetmann

It is certified that error appears in the above—identified patent and that said Letters Patent is hereby corrected as shown below:

Col. 3, line 9; "Advantagdous" should read -- Advantageous --

Col. 6, line 4; insert a -- , -- after the word "weight"

Col. 11, line 1; "hold" should read -- mold --

Col. 13, line 43; insert a -- , -- after the word "then"

Col. 16, line 56; "aboug" should read -- about --

Col. 18, line 26; "thru-treated" should read -- thus-treated --

Signed and Sealed this

Fourth Day of December 1984

[SEAL]

Attest:

Attesting Officer

GERALD J. MOSSINGHOFF

Commissioner of Patents and Trademarks